United States Patent [19]

Brandt

[11] 4,035,242

[45] July 12, 1977

[54] DISTILLATIVE PURIFICATION OF ALKANE SULFONIC ACIDS

[75] Inventor: Donald R. Brandt, Corpus Christi, Tex.

[73] Assignee: PPG Industries, Inc., Pittsburgh, Pa.

[21] Appl. No.: 617,477

[22] Filed: Sept. 29, 1975

[51] Int. Cl.² ..................................... C07C 143/02
[52] U.S. Cl. ................................. 203/15; 203/80; 260/513 R
[58] Field of Search ................. 203/15, 14, 73, 78, 203/80, 91, 94, 98; 260/502, 513, 400

[56] References Cited

U.S. PATENT DOCUMENTS

| | | | |
|---|---|---|---|
| 2,285,337 | 6/1942 | Kapp | 203/80 |
| 3,509,206 | 4/1970 | Nielsen | 260/502 R |

OTHER PUBLICATIONS

The Condensed Chemical Dictionary 8th Ed. Hanley van Nostrand Reinhold N. Y. 1971.

*Primary Examiner*—Hiram N. Bernstein
*Attorney, Agent, or Firm*—Irwin M. Stein; Roger S. Benjamin

[57] ABSTRACT

Aqueous solutions of methane sulfonic acid are dehydrated and purified in a two-step fractionation process.

7 Claims, 1 Drawing Figure

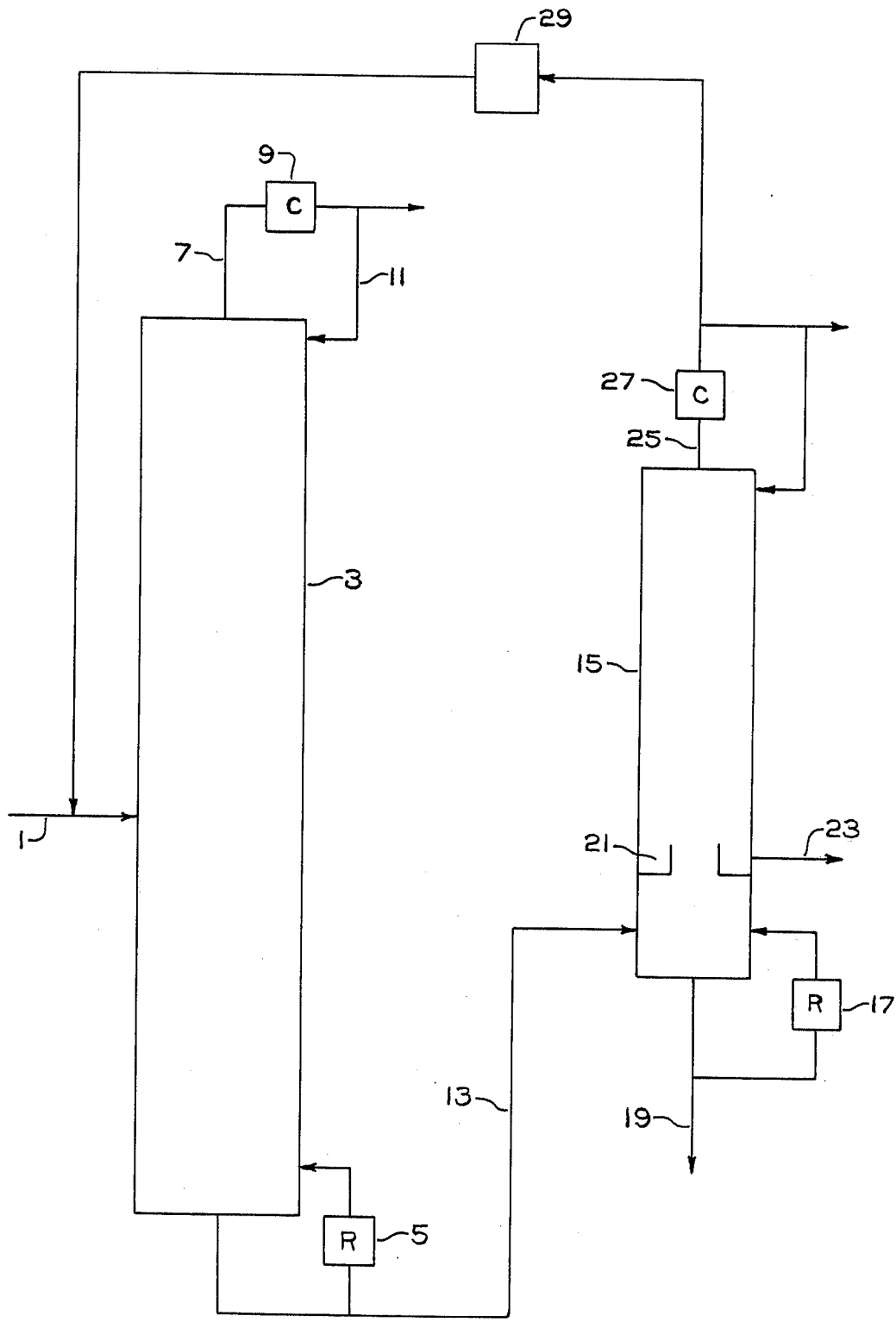

DISTILLATIVE PURIFICATION OF ALKANE SULFONIC ACIDS

BACKGROUND OF THE INVENTION

Aromatic peroxy acids may be prepared from the reaction of hydrogen peroxide and aromatic acids by using a reaction medium of alkane sulfonic acid as described in U.S. Pat. No. 3,143,562.

Inherent in the reaction of aromatic acids and hydrogen peroxide is the formation of by-product water, together with water accompanying the reagents, notably the hydrogen peroxide reactant (hydrogen peroxide is commercially available at 90 weight percent or less concentration). Generally, the best yields of peroxy acids are favored by minimizing the concentration of water in the reaction medium. Thus, it is important to process the alkane sulfonic acid used as reaction medium to remove the greater portion of contained water. It is also economically and environmentally desirable to recycle the alkane sulfonic acid.

Alkane sulfonic acids such as methane sulfonic acid have high boiling points which make simple distillative dehydration unattractive because of attendant decomposition. Recourse to distillation at subatmospheric pressures is usually required to separate water from aqueous alkane sulfonic acid solutions without undue decomposition where reconstitution is required.

THE INVENTION

Condensed methane sulfonic acid (above 98 weight percent acid) withdrawn from the vapor phase of a vacuum distillation apparatus was found to contain methyl methane sulfonate, a decomposition by-product with reported mutagenic activity. It was determined that methyl methane sulfonate was not present (detection limit <0.002 weight percent) prior to distillation, but that its presence was the consequence of formation encouraged by conditions encountered during distillation.

It is an essential aspect of the process of this invention that thermal decomposition of alkane sulfonic acid is minimized by (1) operating a first step distillative dehydration under conditions where the major part of the alkane sulfonic acid is not heated to above its temperature of vaporization and (2) thereafter, in a second step vaporizing a major part of the alkane sulfonic acid in a manner such that a liquid acid product stream is recovered.

It has been discovered that substantially pure substantially anhydrous alkane sulfonic acids such as methane sulfonic acid, ethane sulfonic acid or other lower alkane sulfonic acids may be obtained by recourse to a specially selected combination and sequence of fractionating operations operated at selected temperatures and pressures and employing columns containing rectifying and stripping sections. In particular, it has been found that aqueous methane sulfonic acid compositions containing upwards of 10 weight percent water may be conveniently dehydrated in two sequential fractionation steps, each step of which is conducted under different conditions, so as to reduce formation of alkane sulfonic acid decomposition products such as tars and sulfuric acid and realize a lower alkane sulfonic acid product containing less than 2.0 weight percent water. The conditions of the process of this invention are such that dehydrated methane sulfonic acid containing less then 0.05 weight percent methyl methane sulfonate (MMS) may be prepared.

BRIEF DESCRIPTION OF THE DRAWINGS

The FIGURE is a diagrammatic illustration of a system which may be suitably employed to conduct the process as hereinafter described.

DETAILED DESCRIPTION OF THE INVENTION

The aqueous methane sulfonic acid fed to the first step contains more than 10 weight percent and more normally 25 to 75 weight percent alkane sulfonic acid (the balance being practically considered as water). More dilute acids may be dehydrated in the first step fractionation column but the removal of large volumes of water from very dilute feed is more effectively performed by a pretreatment concentration operation such as flash distillation. Operation of the first step is achieved by feeding aqueous alkane sulfonic acid into an intermediate point of a first column between a liquid bottoms outlet and an overhead vapor outlet, and operating the column under conditions of temperature and subatmospheric pressure such that a stripped liquid bottoms containing more than 4 and less than 10 weight percent water is obtained and withdrawn. From the rectification region above the feed level, vapors, predominantly water vapor are withdrawn as overhead. The fractionation operation performed in the first column serves to separate the majority of the contained water from the aqueous methane sulfonic acid.

Thus, the first column in the process of this invention is operated in a manner such that the portion thereof above the level of the feed (which is at an intermediate level) operates as a rectification section. This rectification section tends to provide water vapor at its uppermost column output and concentrated liquid alkane sulfonic acid composition at its bottom outlet.

Heat is conveniently supplied to the first column by a system such as circulating reboiler at the column base. A minor proportion of acid in the column bottoms may be vaporized to heat the column. The major portion of first column bottoms containing methane sulfonic acid and higher boiling impurities is withdrawn as a liquid and forwarded to the second part of the process.

The composition of the first column concentrator bottoms product is a function of temperature and pressure. A balance of desirable pressure and temperature parameters is selected to yield a liquid bottoms product containing more than four but less than ten weight percent water. Too low a pressure will unnecessarily increase the overhead vapor volume (water) in the first step and reduce the rate of water removal from the column. Conversely, too high a temperature will encourage decomposition of the alkane sulfonic acid to give tars, $H_2SO_4$ and alkyl alkane sulfonate. Acceptable aqueous methane sulfonic acid (MSA) bottoms product in the first step fractionator is obtained by operation at moderate vacuum (100 to 500 mm. Hg) and temperatures between 171° and 186° C. Illustrative combinations of temperature and pressure are shown in Table 1 below.

TABLE 1

| Pressure (mm. Hg) | Wt. % MSA in Bottoms Products | | | |
|---|---|---|---|---|
| | 176° C. | 179° C. | 181° C. | 185° C. |
| 280 | 90 | — | — | — |
| 237 | — | — | — | — |
| 233 | — | — | — | 95 |
| 232 | — | — | 92 | — |

TABLE 1-continued

| Pressure (mm. Hg) | Wt. % MSA in Bottoms Products | | | |
|---|---|---|---|---|
| | 176° C. | 179° C. | 181° C. | 185° C. |
| 187 | — | 95 | — | — |

The second fractionation step is operated to dehydrate, concentrate and purify the liquid bottoms of the first step and yield an alkane sulfonic acid composition containing less than 2 weight percent and preferably less than 1.5 weight percent water.

Operation of the second step fractionation entails feeding the bottoms of the first process step to the lower portion of a second fractionation column; and withdrawing in the second column as overhead vapors, water, "light" impurities such as methyl methane sulfonate (in the processing of methane sulfonic acid), and some volatilized alkane sulfonic acid; withdrawing as bottoms high boiling residues such as sulfuric acid and tars and; withdrawing purified condensed liquid rectified alkane sulfonic acid at a level in the column above the feedpoint.

The liquid alkane sulfonic acid condensed in the rectification section of the second step column may be collected and withdrawn by an appliance such as a liquid product draw tray. The water content (conversely, the acid concentration) of the liquid alkane sulfonic acid product will be determined by its equilibrium with the ascending vaporized acid feedstock from the column bottoms. Therefore, the desired low water content of the product is obtained by vaporizing that concentration of acid which is in equilibrium with a condensed liquid alkane sulfonic acid composition of the desired strength.

In the operation of the process of this invention, the collected liquid purified and concentrated alkane sulfonic acid is withdrawn as a product from the second step fractionation column. The fact that alkane sulfonic acid in the vapor phase is in equilibrium with a relatively higher concentration of liquid acid permits the vaporization of a "weaker" acid in the bottoms of the second column if the product stream is withdrawn as a liquid rather than when the alkane sulfonic acid is directly withdrawn as a vapor phase. In consequence of vaporizing a weaker alkane sulfonic acid, a lower temperature with reduced attendant decomposition is possible.

Heat for second column fractionation is conveniently provided by a reboiler at the column base. The second column operation requires vaporization of the major part of the alkane sulfonic acid in the bottoms to raise the alkane sulfonic acid into the rectification region of the column and permit its transfer to the liquid draw outlet.

The second of the two column is generally operated at lower pressures than first column to reduce the temperatures required to vaporize the alkane sulfonic acid. The second column is operated under such conditions of temperature and subatmospheric pressure such that a major part of feed is vaporized and a rectified liquid alkane sulfonic acid collected above the feedpoint. For example, second column pressures of 1 to 60, preferably 15 to 20 Torr are employed. The corresponding temperature of the bottoms fraction is about 188° C. to 205° C.

The two part distillation dehydration system employs usual accessories such as valves, pumps, condensers and heat exchangers. Provision may be made to recirculate a portion of the overhead or bottoms fractions to obtain greater purification. The extremely corrosive nature of alkane sulfonic acids requires that all materials of construction in the system be acid resistant (e.g., glass).

It is desirable to achieve close contact between the ascending vapors and descending liquid alkane sulfonic acid in both parts of the process. To facilitate such contact, the column may be filled with packing such as plates, screens, rings, or the like.

The first and second part columns need not be limited to a single piece of apparatus. For example, a bank of columns operating in parallel may be employed. The fractionating "column" employed in each of the two parts of this process is not confined to the shape of a right circular cylinder. If desired, "columns" having geometries with varying cross-sectional areas may be used, for example, to permit improved vapor transfer rates.

In practice, the overhead vapor from the second part of the process may contain appreciable alkane sulfonic acid. This dilute acid may be concentrated and recycled to the fractionation process.

Methane methyl sulfonate which accumulates may be destroyed by an additional hydrolysis step. Hydrolysis is effected by storage at elevated temperatures for a period of time (typically, above 50° C. for over 8 hours).

In general, the second step column will be of smaller dimensions than the first step column in consequence of the smaller volume of feedstock.

This invention will be more clearly understood from the following detailed description made in conjunction with the diagrammatic illustration of the FIGURE.

Dilute methane sulfonic acid feed having an acid content between 50 and 75 weight percent is charged via feedline 1 to a first step concentrator in the form of a packed column 3. The first column is heated to a temperature between 174° C. and 180° C. in circulating reboiler 5 and the column pressure adjusted to between 200 to 400 mm. Hg. Water is withdrawn as vapor at overheat outlet 7 and cooled by condenser 9. The major portion of condensed overhead is sewered and a minor portion of the overhead vapor is refluxed to the upper portion of the column via line 11 to enhance separation of water from the rectified acid feed.

Stripped liquid methane sulfonic acid of 92 to 96 weight percent acid concentration (together with high boiling and insoluble residues) flows through the stripping zone below the feedline 1 in column 3 via line 13 to the second part distillation column 15. The major portion of concentrated acid fed to column 15 is vaporized in reboiler 17 at temperatures from 192° C. to 200° C. and pressures of 10 to 30 mm. Hg. Accumulated decomposition residues of sulfuric acid and tars are disposed of through line 19. Methane sulfonic acid vapor is rectified and recondensed as a liquid having one and one-half weight percent water on liquid produce draw tray 21 for removal through line 23. Overhead water vapors and some vaporized alkane sulfonic acid is removed via line 25 and liquefied in condenser 27. Hydrolysis tank 29 retains condensed overhead from line 25 for 8 hours at a temperature of 50° C. to decompose isolated methyl methane sulfonate. The treated acid stream from tank 29 is recycled to column 3. The process is operated so that aqueous methane sulfonic acid feed is fed to the first step and withdrawn from the second step on a continuous basis.

EXAMPLE

This example illustrates the practice of the invention. A two-step fractionation of aqueous methane sulfonic acid (MSA) was conducted using a concentrator fractionation column followed by a liquid draw product fractionation column. The first column concentrator was a six foot tall, six inch diamater glass tube packed with ballast rings in the upper five-sixths of its height. Twenty-one thousand four hundred and forty-four pounds of aqueous feed averaging 61.8 weight percent methane sulfonic acid, 0.22 percent methyl methane sulfonate (MMS), and 0.18 percent $H_2SO_4$ (the balance being water) were fed to the first column at a feed rate of up to about 60 pounds per hour under the following conditions:

TABLE 2

| Operating Conditions | First Column Concentrator |
|---|---|
| Column Pressure, mm. Hg. Abs. | 235 |
| Pressure Drop, mm. Hg. | 15 |
| Top Temperature, ° C. | 80 |
| Reboiler Temperature, ° C. | |
| In | 175–180 |
| Out | 175–180.5 |

The analysis of the first column fractionation is as follows:

TABLE 3

| | Wt. % MSA | Wt. % MMS Range | Wt. % MMS Average | Wt. % $H_2SO_4$ |
|---|---|---|---|---|
| Feed | 61.8 ± 13.9 | < .1 – .57 | 0.22 ± .15 | 0.18 ± 9.19 |
| Overheads | 2.34 | 0.01 – 0.14 | 0.07 | < 0.02 |
| Bottoms | 94.1 ± 2.1 | < 0.01 – 0.95 | 0.25 ± 0.22 | 1.04 ± 0.96 |

The first column bottoms were fed at a rate of about 42 pounds per hour to a second 6 foot long, 6 inch diameter glass distillation column packed with ballast rings in the upper two-thirds of its height. The column was equipped with a liquid product draw tray two feet from its base. Operating conditions of the second column were as follows:

TABLE 4

| Operating Conditions | Product Still |
|---|---|
| Column Pressure, mm. Hg. Abs. | 15–20 |
| Pressure drop, mm. Hg. | 10 |
| Top Temperature, ° C. | 160 |
| Draw Temperature, ° C. | 185–188 |
| Reboiler Temperature, ° C. | |
| In | 193–199 |
| Out | 194–200 |

The second column fractionation gave products of the following analysis:

TABLE 5

| | Wt. % MSA | Wt. % MMS Range | Wt. % MMS Average | Wt. % $H_2SO_4$ |
|---|---|---|---|---|
| Feed[1] | 95.4 ± 2.8 | < 0.01 – 0.95 | 0.20 ± 0.21 | 0.66 ± 0.8 |
| Overheads | 62.9 ± 11.0 | 0.01 – 0.5 | 0.33 ± 0.17 | < .02 |
| Bottoms[2] | 87.4 ± 8.9 | 0.6 – 3.2 | 1.64 ± 0.85 | 5.7 ± 5.1 |
| Product | 98.89 ± 0.54 | < 0.02 – 0.37 | 0.08 ± 0.07 | 0.46 ± 0.43 |

[1]The second column feed had a higher acid concentration than the bottoms product of the first column because less dilute recycle acid was in the system.
[2]MSA concentration in first column bottoms is higher than in second column bottoms due to loss of MSA to MMS and $H_2SO_4$ formation.

The liquid draw tray product has low water (not more than 1.65 weight percent) and very low methyl methane sulfonate values. Methyl methane sulfonate which formed has been segregated in the overhead and bottoms fractions. In addition, total losses of methyl sulfonate acid by decomposition to methyl methane sulfonate and $H_2SO_4$ are relatively low.

It will be understood that various changes and modifications can be made in details of the described distillative methane sulfonic acid purification process without departing from this invention, and that all changes are intended to be included within the scope of the claims.

I claim:

1. A process for preparing lower alkane sulfonic acid having a water content of less than 2 weight percent by feeding aqueous alkane sulfonic acid having a water content greater than 10 weight percent into a first fractionating column feedline intermediate between a liquid bottoms outlet and an overhead vapor outlet thereof; operating said first column under conditions of temperature and subatmospheric pressure such that a major part of the so fed alkane sulfonic acid is not heated to above its temperature of vaporization and a bottoms product of stripped liquid alkane sulfonic acid containing more than 4 but less than 10 weight percent water is obtained; then feeding said bottoms product from said first column to the lower portion of a second fractionating column, said second column being operated under conditions of temperature and subatmospheric pressure such that the major part of alkane sulfonic acid in said bottoms produce fed thereto is vaporized with rectification and a rectified liquid alkane sulfonic acid having a water content of less than 2 weight percent collected and withdrawn as a liquid from said second column above the feedpoint of said bottoms product.

2. A process according to claim 1 wherein the first column is operated at pressures between 100 to 500 mm. Hg and temperatures between 171° C. and 186° C.

3. A process according to claim 1 wherein the first column is operated at pressures between 200 to 400 mm. Hg and temperatures between 174° C. and 180° C.

4. A process according to claim 1 wherein the second column is operated at pressures between 1 to 60 mm. Hg and temperatures between 188° C. to 205° C.

5. A process according to claim 1 wherein the second column is operated at pressures between 10 to 30 mm. Hg and temperatures between 192° C. and 200° C.

6. A process according to claim 2 wherein the first column feed comprises aqueous methane sulfonic acid.

7. A process according to claim 3 wherein the first column feed contains 50 to 75 weight percent methane sulfonic acid.

* * * * *